(12) United States Patent
Aghassian

(10) Patent No.: US 9,186,520 B2
(45) Date of Patent: Nov. 17, 2015

(54) AUTOMATIC ON-OFF CHARGER FOR AN IMPLANTABLE MEDICAL DEVICE

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 83 days.

(21) Appl. No.: 13/741,097

(22) Filed: Jan. 14, 2013

(65) Prior Publication Data

US 2013/0184785 A1 Jul. 18, 2013

Related U.S. Application Data

(60) Provisional application No. 61/587,002, filed on Jan. 16, 2012.

(51) Int. Cl.
*A61N 1/00* (2006.01)
*A61N 1/378* (2006.01)

(52) U.S. Cl.
CPC .................................. *A61N 1/3787* (2013.01)

(58) Field of Classification Search
CPC ......................................... A61N 1/378–1/3787
USPC .......................................... 607/29, 33–35, 61
See application file for complete search history.

(56) References Cited

U.S. PATENT DOCUMENTS

| 7,444,181 | B2 | 10/2008 | Shi et al. |
|---|---|---|---|
| 7,890,182 | B2 | 2/2011 | Parramon et al. |
| 8,244,367 | B2 | 8/2012 | Wahlstrand et al. |
| 2007/0100399 | A1 | 5/2007 | Parramon et al. |
| 2008/0319475 | A1 | 12/2008 | Griffith et al. |
| 2010/0114241 | A1 | 5/2010 | Donofrio et al. |
| 2010/0305663 | A1 | 12/2010 | Aghassian |
| 2011/0301668 | A1 | 12/2011 | Forsell |
| 2012/0004708 | A1 | 1/2012 | Chen et al. |

(Continued)

FOREIGN PATENT DOCUMENTS

WO      2004/002572 A1      1/2004

OTHER PUBLICATIONS

International Search Report regarding application No. PCT/US2013/021705 dated Apr. 5, 2013.

(Continued)

*Primary Examiner* — Scott Getzow
(74) *Attorney, Agent, or Firm* — Lewis & Reese, PLLC

(57) ABSTRACT

An external charger for an implantable medical device is disclosed which can automatically detect an implant and generate a charging field. The technique uses circuitry typically present in an external charger, such as control circuitry, a Load Shift Keying (LSK) demodulator, and a coupling detector. An algorithm in the control circuitry periodically issues charging fields of short duration in a standby mode. If the coupling detector detects the presence of a conductive material, the algorithm issues a listening window during which a charging field is generated. If an LSK reply signal is received at the LSK demodulator, the external charger can charge the implant in a normal fashion. If a movement signature is detected at the LSK demodulator indicative of a predetermined user movement of the external charger, a charging field is issued for a set timing period, to at least partially charge the IPG battery to restore LSK communications.

34 Claims, 9 Drawing Sheets

(56) References Cited

U.S. PATENT DOCUMENTS

2012/0092031 A1 4/2012 Shi et al.
2012/0095519 A1 4/2012 Parramon et al.
2012/0095529 A1 4/2012 Parramon et al.
2013/0006315 A1 1/2013 Lee

OTHER PUBLICATIONS

U.S. Appl. No. 13/489,770, filed Jun. 6, 2012, Parramon et al.

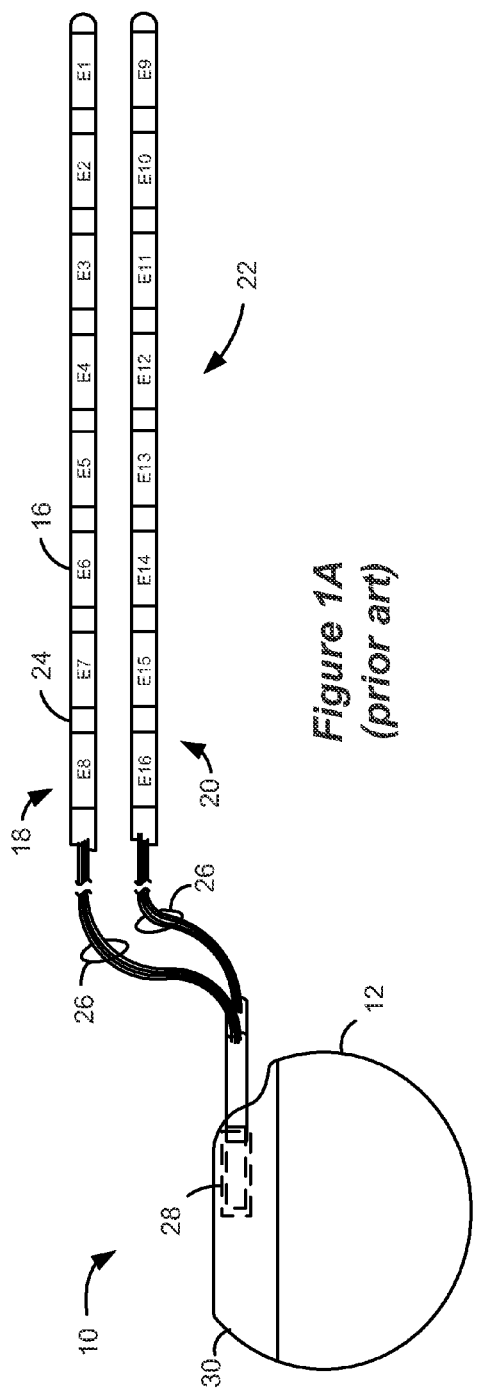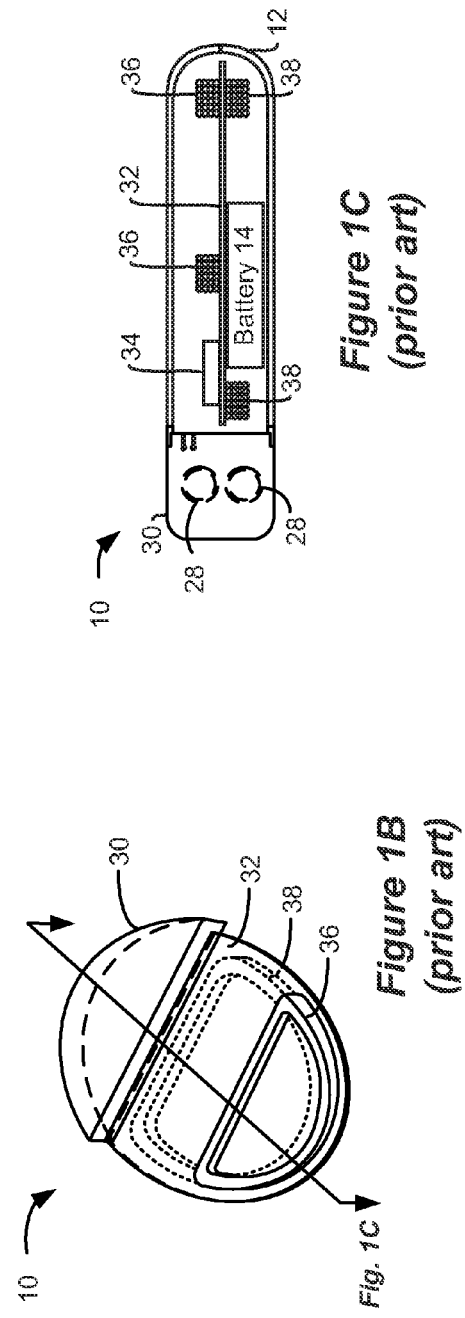

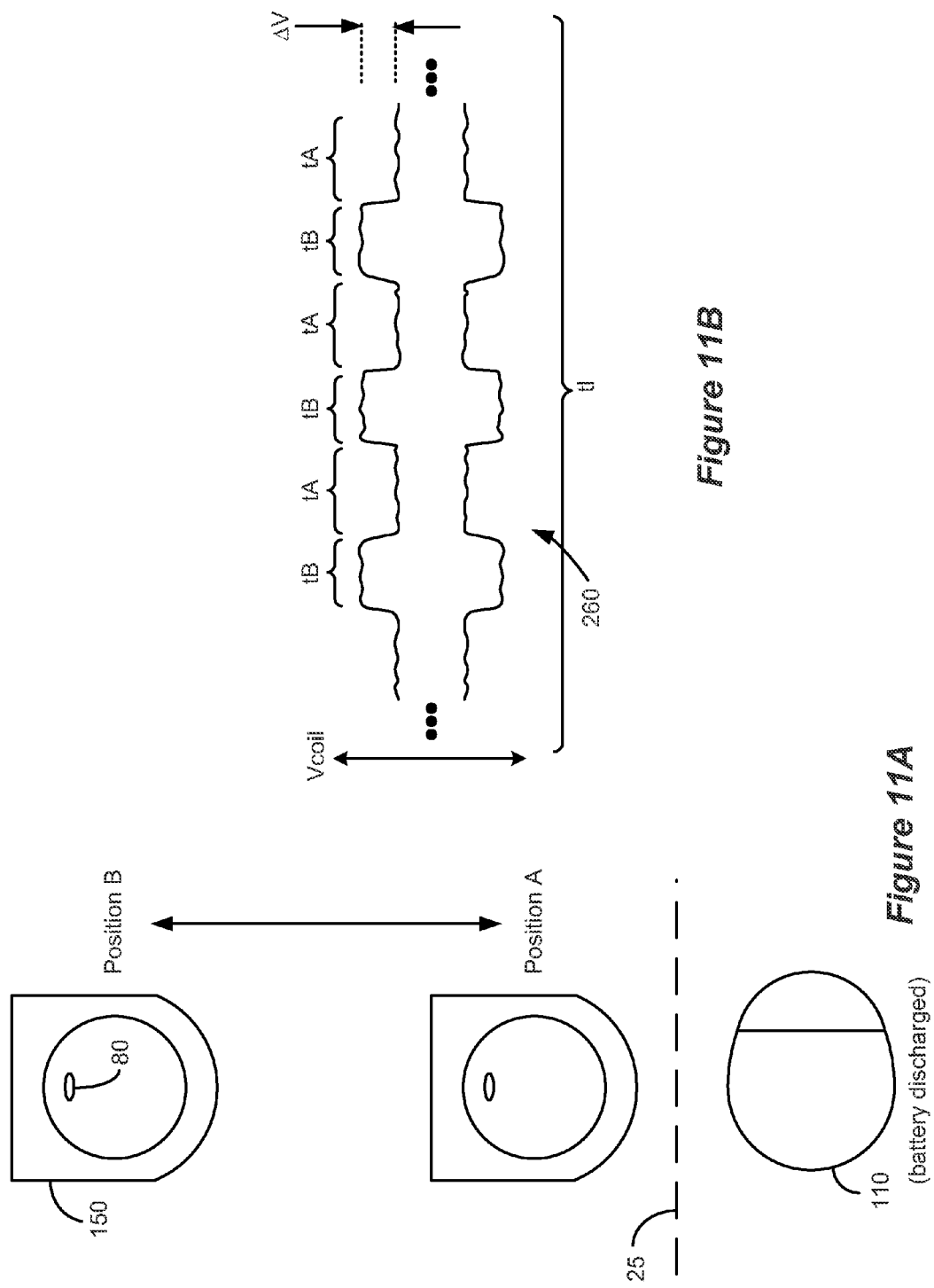

AUTOMATIC ON-OFF CHARGER FOR AN IMPLANTABLE MEDICAL DEVICE

CROSS-REFERENCE TO RELATED APPLICATIONS

This a non-provisional of U.S. Provisional Patent Application Ser. No. 61/587,002, filed Jan. 16, 2012, to which priority is claimed.

FIELD OF THE INVENTION

The present invention relates to wireless external chargers for use in implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A-1C, a SCS system typically includes an Implantable Pulse Generator (IPG) 10, which includes a biocompatible device case 12 formed of a conductive material such as titanium for example. The case 12 typically holds the circuitry and battery 14 necessary for the IPG to function, although IPGs can also be powered via external RF energy and without a battery. The IPG 10 is coupled to electrodes 16 via one or more electrode leads (two such leads 18 and 20 are shown), such that the electrodes 16 form an electrode array 22. The electrodes 16 are carried on a flexible body 24, which also houses the individual signal wires 26 coupled to each electrode. In the illustrated embodiment, there are eight electrodes on lead 18, labeled $E_1$-$E_8$, and eight electrodes on lead 20, labeled $E_9$-$E_{16}$, although the number of leads and electrodes is application specific and therefore can vary. The leads 18, 20 couple to the IPG 10 using lead connectors 28, which are fixed in a non-conductive header material 30, which can comprise an epoxy for example.

As shown in the cross-section of FIG. 1C, the IPG 100 typically includes an electronic substrate assembly including a printed circuit board (PCB) 32, along with various electronic components 34 mounted to the PCB 32, some of which are discussed subsequently. Two coils (more generally, antennas) are generally present in the IPG 100: a telemetry coil 36 used to transmit/receive data to/from an external controller (not shown); and a charging coil 38 for charging or recharging the IPG's battery 14 using an external charger 50. In this example, the telemetry coil 36 and charging coil 38 are within the case 12, as disclosed in U.S. Patent Publication 2011/0112610. (FIG. 1B shows the IPG 10 with the case 12 removed to ease the viewing of the two coils 36 and 38). However, the telemetry coil 36 may also be mounted within the header 30 of the IPG 10 (not shown)).

FIG. 2 shows the IPG 10 in communication with external charger 50 just mentioned. The external charger 50 is used to wirelessly convey power to the IPG 10, which power can be used to recharge the IPG's battery 14. The transfer of power from the external charger 50 is enabled by a coil (antenna) 52. The external charger 50, like the IPG 10, also contains a PCB 54 on which electronic components 56 are placed. Some of these electronic components 56 are discussed subsequently. A user interface, which can include a touchable button 60, an LED indicator 62, a display (not shown) and a speaker (not shown), allows a patient or clinician to operate the external charger 50. A battery 64 provides power for the external charger 50, which battery 64 may itself be rechargeable or replaceable. The external charger 50 can also receive AC power from a wall plug. A hand-holdable case 66 sized to fit a user's hand contains all of the components.

Power transmission from the external charger 50 to the IPG 10 occurs wirelessly and transcutaneously through a patient's tissue 25 via inductive coupling. FIG. 3 shows details of the circuitry used to implement such functionality. For power transmission, control circuitry 70 in the external charger 50 outputs a charging signal (typically, an 80 KHz pulse train) to an amplifier 72 (to "driver circuitry" more generally), which generates a constant AC current Icoil of the same frequency to create an AC magnetic charging field 96. The control circuitry 70 can comprise a microcontroller for example. A capacitor (not shown) is used to tune the resonance of the coil 52 to the frequency of the AC current (e.g., 80 KHz) generated by the amplifier 72. The magnetic field 96 induces a current in the charging coil 38 within the IPG 10, which current is rectified 82 to DC levels, and used to recharge the battery 14, perhaps via a charging and battery protection circuit 84 as shown. When charging the battery 14 in this manner, is it typical that the case 66 of the external charger 50 touches the patient's tissue 25, although this is not strictly necessary.

The IPG 10 can communicate data back to the external charger 50 during charging using reflected impedance modulation, which is sometimes known in the art as Load Shift Keying (LSK). Such back telemetry from the IPG 10 can provide useful data concerning charging to the external charger 50, such as the capacity of the battery 14, or whether charging is complete and the external charger 50 can cease.

Control circuitry 80 in the IPG 10 monitors the battery voltage, Vbat, and with the assistance of LSK modulator 86, produces LSK data. The control circuitry 80 can include a microcontroller for example, and may be associated with Analog-to-Digital (A/D) conversion circuitry to process and interpret the battery voltage. The control circuitry 80 assesses the incoming battery voltage to produce appropriate LSK data at appropriate times. Such LSK data is sent as a serial string of bits to the gate of transistor 88. The LSK data modulates the state of transistor 88, which in turn modulates the impedance of the coil 38. When LSK data=1, the transistor 88 is on (closed) which shorts the coil 38. When LSK data=0, the transistor 88 is off (opened). (Also shown in FIG. 3 are the Frequency Shift Keying (FSK) modulation 92 and demodulation 90 telemetry circuitry coupled to telemetry coil 36, which as noted above, are typically used to communicate with an external controller (not shown)).

Such modulation of the charging coil 38 is detectable at the external charger 50. Due to the mutual inductance between the coils 52 and 38, any change in the impedance of coil 38 affects the voltage needed at coil 52, Vcoil, to drive the prescribed charging current, Icoil: if coil 38 is shorted (LSK data=1), Vcoil increases to maintain Icoil; if not shorted (LSK data=0), Vcoil decreases. In this sense, the impedance modulation of coil 38 is "reflected" back to the charging coil 52, and thus data can be said to be "transmitted" from the IPG 10 to the external charger 50, even if not transmitted in the traditional sense.

Changes in Vcoil are sensed at LSK demodulation circuitry 74 to recover the transmitted LSK data. The serial stream of demodulated bits is then received at control circuitry 70 so that appropriate action can be taken. For example, if the LSK modulation circuitry 86 in the IPG 10 transmits an alternating stream of bits (01010101 . . . ), this might be interpreted by the control circuitry 70 as a stop charging signal, i.e., a signal indicating that the battery 14 in the IPG 10 is full, and therefore that charging can cease. In such an instance, the control circuitry 70 can suspend the production of the magnetic charging field 96 (i.e., setting Icoil to 0), and may notify the user of that fact (by a graphical display, an audible beep, or other indicator).

An issue arising when inductive coupling is used for power transmission relates to the coupling between the coils 52 and 38 in external charger 50 and the IPG 10. Coupling, generally speaking, comprises the extent to which power expended at the transmitting coil 52 in the external charger 50 is received at the coil 38 in the IPG 10. It is generally desired that the coupling between coils 52 and 38 be as high as possible: higher coupling results in faster charging of the IPG battery 14 with the least expenditure of power in the external charger 50. Poor coupling is disfavored, as this will require high power drain (i.e., a high Icoil) in the external charger 50 to adequately charge the IPG battery 14. The use of high power depletes the battery 64 (if any) in the external charger 50, and more importantly can cause the external charger 50 to heat up, and possibly burn or injure the patient.

Coupling depends on many variables, such as the permeability of the materials used in the external charger 50 and the IPG 100, as well materials inherent in the environment. Coupling is also affected by the relative positions of the external charger 50 and IPG 10. The control circuitry 70 uses a coupling detector 76 to detect the alignment or proximity between the external charger 50 and the IPG 10. Typically, the coupling detector 76 includes circuitry that can measure the amplitude of the voltage across the coil 17, which amplitude can be used as an indicator for the degree of proximity and alignment between the external charger 50 and the IPG 10. Coupling detectors 76 are known in the art, and are therefore not discussed in detail here. Additional details concerning alignment detection can be found in commonly owned U.S. Provisional Application No. 61/546,850, filed Oct. 13, 2011 entitled "Charger Alignment in an Implantable Medical Device System Employing Reflected Impedance Modulation."

Generally, the control circuitry 70 in the external charger 50 indicates misalignment to a user via an alignment indicator 78. Often, the alignment indicator 76 comprises a speaker (not shown) for issuing an audible indication such as a "beep" for example when the external charger 50 is misaligned with the IPG 100. (Alternately, a "beep" could indicate an aligned condition). Alignment indicator 78 can also comprise a visual indicator such as a display or a lamp (e.g., LED 62) on the external charger 50, or a tactile indicator such as a vibration motor that causes the external charger 50 to vibrate. (An audible or tactile indication would be preferred if the external charger 50 isn't easily viewed by the patient during a charging session). Upon hearing, seeing, or feeling (or failing to see, hear, or feel) such an indication, the user of the external charger 50 can use his or her hand to then laterally shift the position of the external charger 50 until better alignment with the IPG 10 is achieved, and the indicator ceases (or issues).

FIG. 4 shows the user interface of the external charger 50. As previously mentioned, the user can turn on/off the charging field 96 by pressing the switch 60. The inventor recognizes drawbacks to having an on/off switch 60 on the charger 50, which drawbacks include increased cost of external charger 50, increased size of user interface, reduced reliability of external charger 50, increased weight of external charger 50, etc.

Solutions have been proposed to allow an external charger to automatically detect when an implant is in its vicinity, and to start charging automatically. For example, in U.S. Patent Application Publication 2009/0112291, an external charger is disclosed that exchanges telemetry with an implant to determine whether charging should begin. In the '291 Publication, the external charger periodically telemeters to the implant requests to begin charging. If the implant is in the vicinity of the external charger, it can receive these requests, and can reply back to the external charger, which can then begin generating a changing field. During charging, the external charger can periodically suspend the charging field to allow the implant to telemeter battery status information, which can allow the external charger to cease producing a changing field once the battery in the implant is fully charged.

The inventor finds the means disclosed in the '291 Publication for automatically determining implant vicinity and automatically beginning charging to be less than optimal, as it requires the external charger to have additional hardware, namely a telemetry transmitter and receiver, and an associated antenna, that are not normally present in an external charger, and which are separate from the external charger's charging coil. Requiring such additional hardware increases the cost and complexity of the external charger.

Additionally, the technique disclosed in the '291 Publication would be ineffective if the battery in the implant has become so depleted that it is unable to operate. If that occurs, the implant would not have enough power to resolve the periodic request signals from the external charger, nor to reply back to the external charger. The external charger would thus conclude that the IPG is not present, and would not provide a charging field, even though the implant clearly needs charging in this circumstance.

It is therefore desired by the inventor that an external charger be able to automatically begin and suspend charging in a solution that does not require substantial modification to the hardware normally present in an external charger, even when the implant battery is depleted, and this disclosure provides such solutions.

BRIEF DESCRIPTION OF THE DRAWINGS

FIGS. 1A-1C show different views of an implantable medical device, specifically an Implantable Pulse Generator (IPG).

FIGS. 11A and 11B show how moving the external charger can be used to indicate its proximity to the IPG during the listening window.

DETAILED DESCRIPTION

An improved external charger is disclosed, which external charger does not require a switch to turn on or off the charging field to provide power to the IPG. The external charger automatically determines whether it is proximate to the IPG, and if so can begin charging. This determination doesn't require additional telemetry circuitry (such as FSK telemetry circuitry) in the external charger, but instead relies on circuitry generally already present in an external charger, such as control circuitry, a Load Shift Keying (LSK) demodulator, and a coupling detector. An on/off algorithm in the control circuitry periodically issues charging fields of short duration in a power-saving standby mode. If the coupling detector detects the presence of a conductive material, which might be the IPG requiring charging, the on/off algorithm issues a listening window during which a charging field is generated. If an LSK reply signal is received at the LSK demodulator from the IPG during the listening window, the external charger can continue charging in a normal fashion. Alternatively, if a movement signature is detected at the LSK demodulator, indicative of user movement of the external charger relative to the IPG, a charging field is issued for a set timing period, with the hope of at least partially charging the IPG battery to the point where LSK communications are restored. If neither indication is detected, the external charger enters a standby mode to save power, which mode is exited only if the external charger senses a change in its position.

Figure 2:
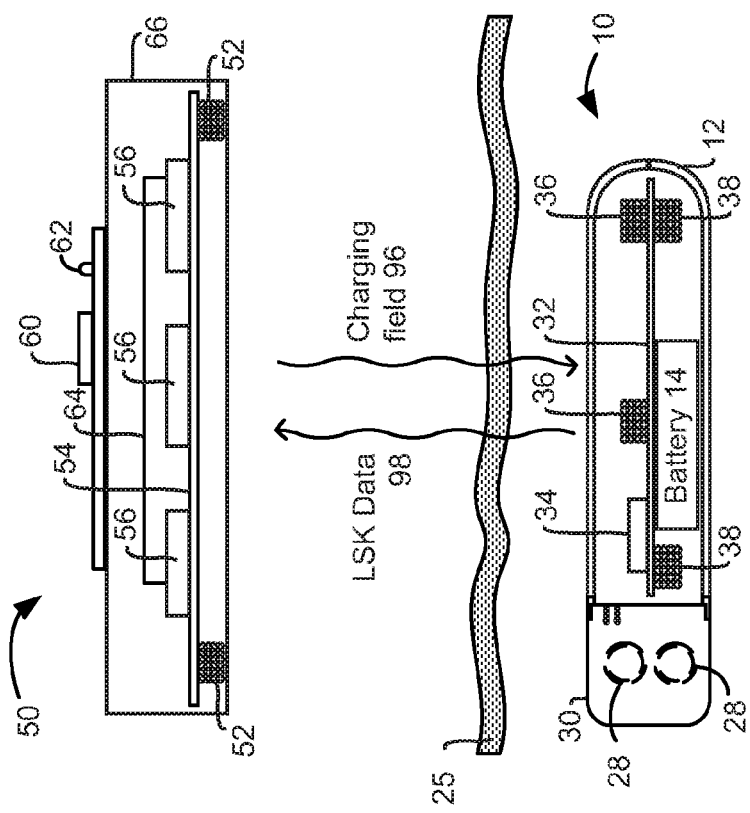
FIG. 2 shows wireless links between the IPG and an external charger.
Figure 3:
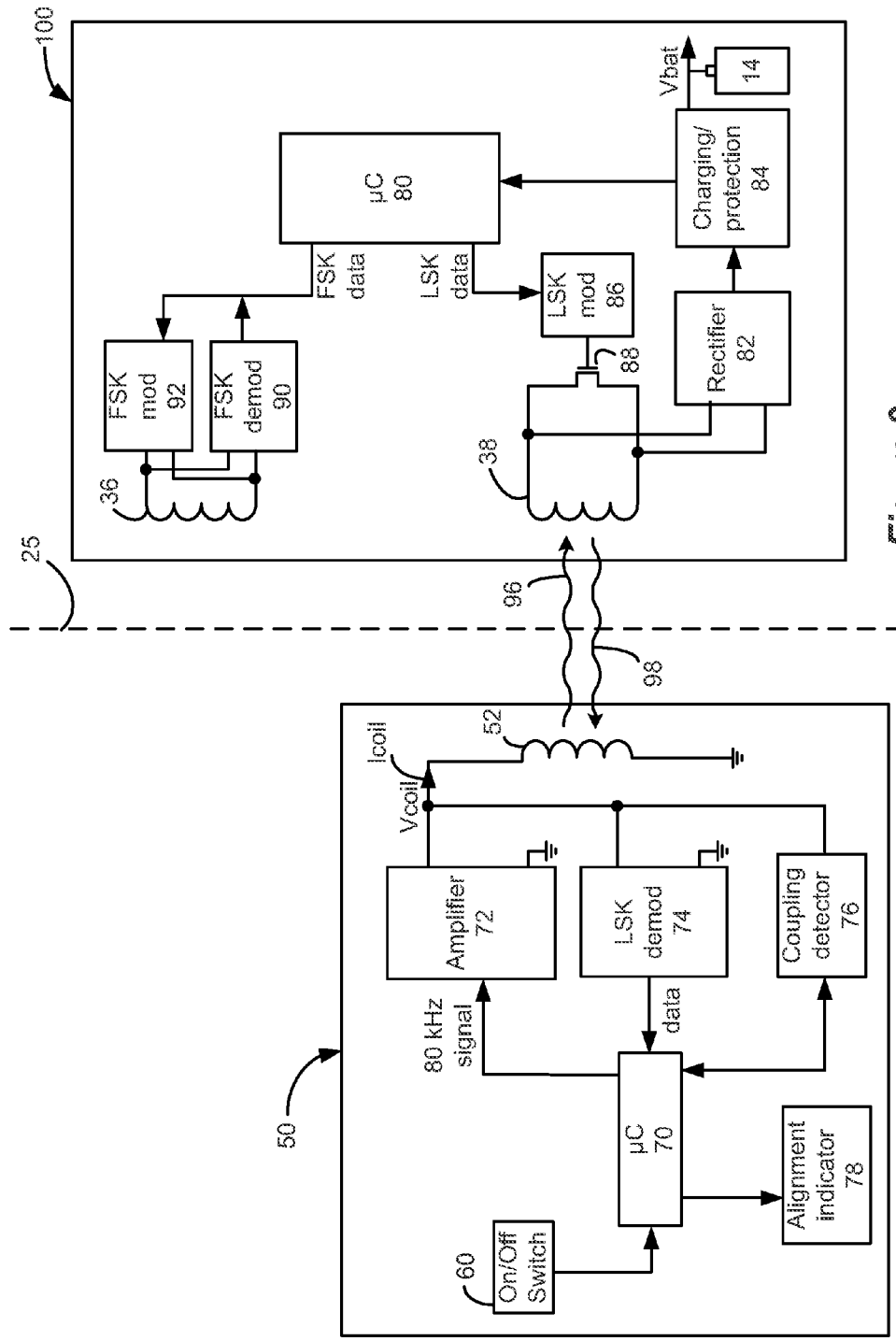
FIG. 3 shows circuitry in both the IPG and external charger for providing power to the IPG.
Figure 4:
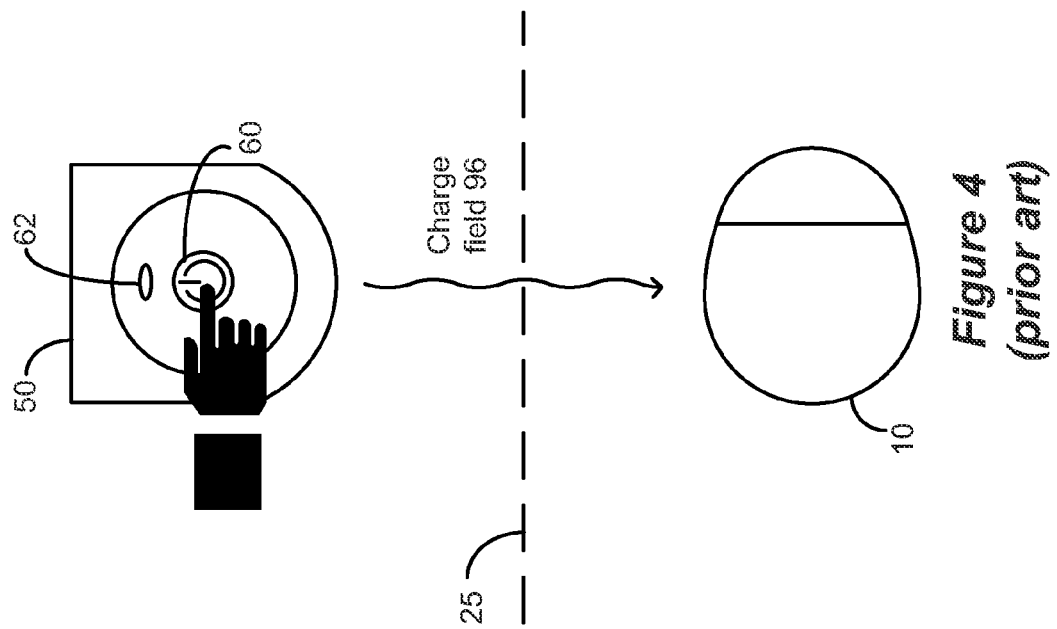
FIG. 4 shows turning on/off of the external charger by using an on/off switch.
Figure 5:
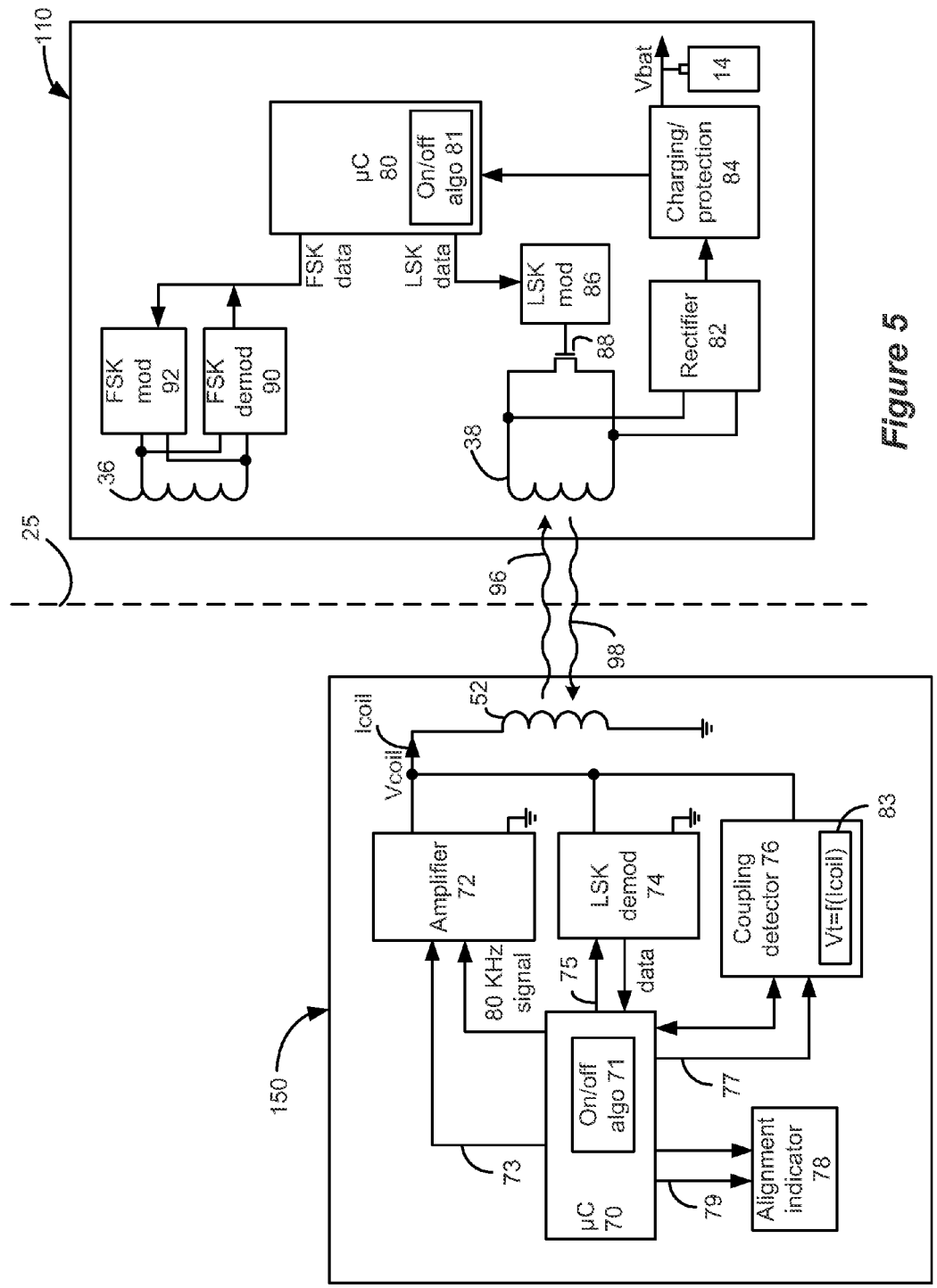
FIG. 5 shows improved circuitry for an external charger system in which the external charger does not have an on/off switch, including programmed on/off algorithms for automatically charging the IPG.

Circuitry for the improved external charger 150 is disclosed in FIG. 5. In contrast with the prior art external charger 50 (FIG. 3), the external charger 150 does not include an on/off switch 60 for turning on/off the charging field 96. Instead, the control circuitry 70 is programmed with an on/off algorithm 71 that operates to automatically detect when an IPG 110 is present, and to generate a charging field 96 to charge the IPG 110's battery 14. An on/off algorithm 81 programmed in the control circuitry 80 of the IPG 110 complements operation of the on/off algorithm 71 in the external charger 150, as explained further below.

Figure 6:
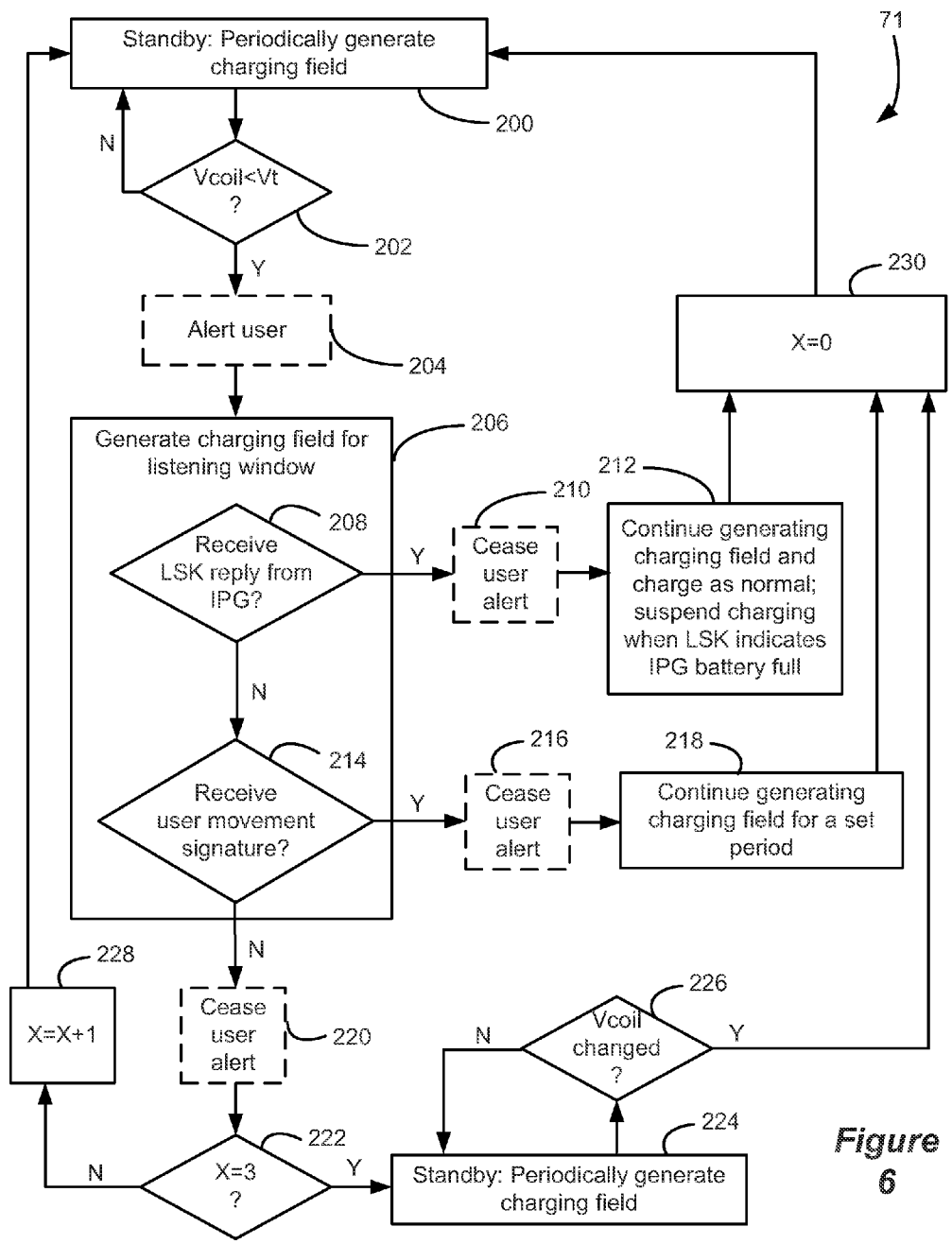
FIG. 6 shows an example of the on/off algorithm for use in the external charger.
Figure 7:
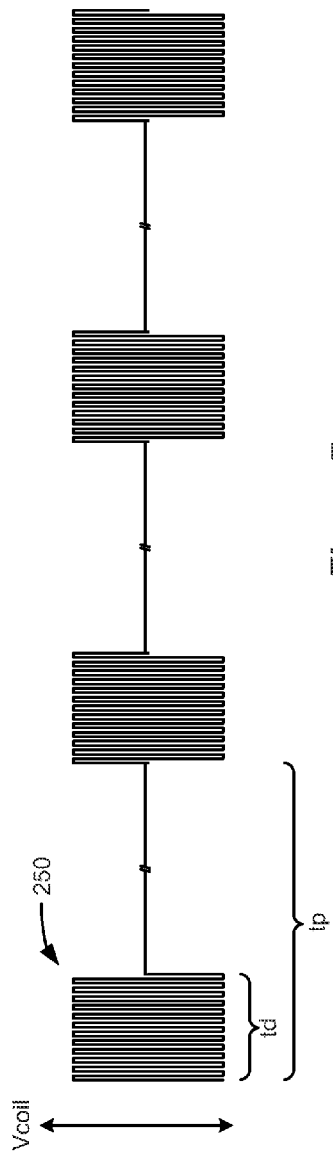
FIG. 7 shows the standby mode for the external charger, in which short duration charging field periods are issued.

An embodiment of on/off algorithm 71 is shown in flow chart form in FIG. 6. As shown, the external charger 150 periodically generates a magnetic charging field 96 in a standby mode (step 200). These periods 250 are shown in FIG. 7 from the perspective of the voltage on coil 52, Vcoil. The charging field periods 250 are of short duration, td, during which time Vcoil will oscillate. The short duration charging field periods 250 are produced with a period, tp. In one example, td can equal approximately 1 millisecond, and tp can equal approximately 1 second. Notice that during the standby mode (step 200), the external charger 150 is only producing a charging field 0.1% of the time. While generating a charging field 96 during these periods will expend some energy in the external charger 150, such expenditure is tolerable: power in the external charger 150 is not critical, because it is relatively easy to replace or charge the battery 64 in the external charger.

Enable signals 73, 75, 77, and 79 (FIG. 5) can be issued by the control circuitry 70 to turn off the various circuit blocks (e.g., the amplifier 72, the LSK demodulator 74, the coupling detector 76, and the alignment indicator 78) between the periods 250 that the external charger 150 is providing a charging field 96. One skilled in the art will understand that such circuit blocks can be disabled by disconnecting the block from the power supply using a switch, although this isn't shown.

Figure 8:
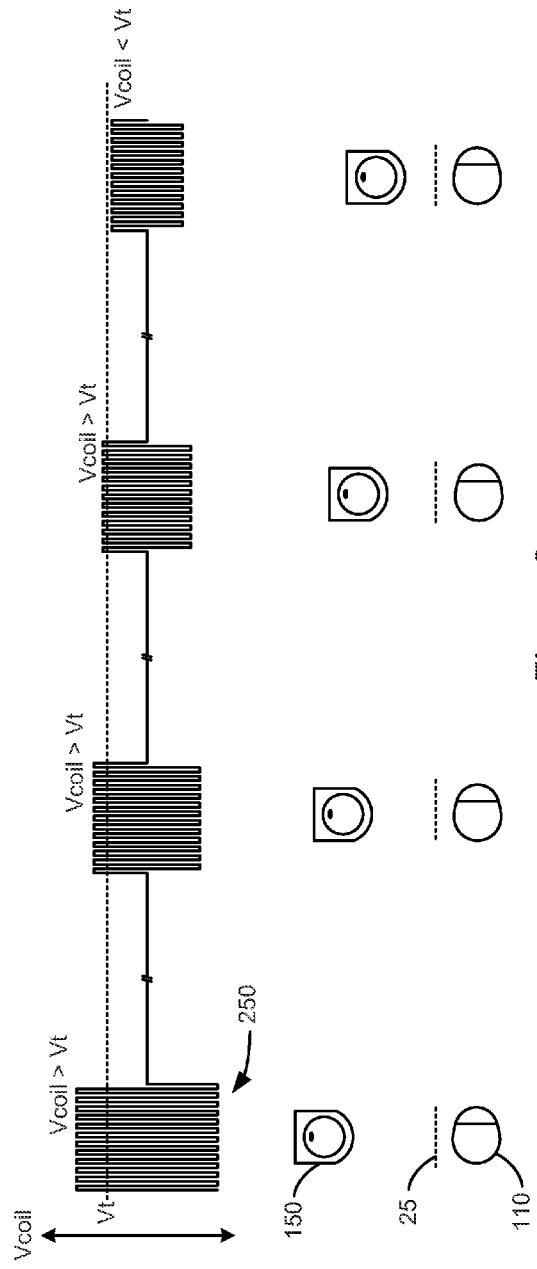
FIG. 8 shows how the magnitude of the coil voltage in the external charger during the periods can be used to infer external charger proximity to the IPG or other conductive structure.

During the standby mode, the external charger 150 attempts to sense whether an IPG requiring charging could be in its vicinity by assessing Vcoil, as shown in FIG. 8. Specifically shown is how Vcoil changes as the external charger 150 is brought closer to the IPG 110 during each successive periodic generation of the charging field 96. As shown, Vcoil decreases as the external charger 150 approaches the IPG 110. This occurs because of mutual inductance: the coil 52 in the external charger 150 is loaded by the conductive elements in the IPG 110, most significantly the IPG's conductive case 12. Specifically, the magnetic charging field 96 will generate eddy currents in the conductive case 12 and other conductive structures in the IPG, which eddy currents produce an opposing magnetic field, making it easier for the external charger 150 to generate the prescribed constant Icoil current through the coil 52. As a result, Vcoil drops, which can be sensed at the coupling detector 76. Eventually, Vcoil will drop below a threshold, Vt, which threshold Vt can be programmed 83 (FIG. 5) into the coupling detector 76. When this occurs (step 202), the coupling detector 76 can indicate to the on/off algorithm 71 that an IPG 110 may be present, and thus that further steps in the algorithm can commence. One skilled will understand that although Vcoil varies throughout any given period 250 (e.g. at 80 kHz), the maximums within each period can be integrated or averaged to determine a singular Vcoil for each period. If Vcoil is not less than Vt (step 202), the algorithm 71 returns to the standby mode (step 200) to assess Vcoil of future periods 250 relative to the Vt.

Choosing the correct Vt for use in the coupling detector 76 will likely be based on experimentation, i.e., that point at which the designers of the system determine that a particular IPG 110 is suitably coupled to the external charger 150 to be able to significantly receive the charging field 96 the external charger 150 produces. The relevant threshold Vt will be dependent on the charging current, Icoil, used by the external charger 150 at any given moment. Again, experimentation can yield the Vt v. Icoil data 83 necessary for the external charger 150.

To prevent inadvertent charging, and needless progression through the on/off algorithm 71, the coupling detector 76 may not issue that the threshold Vt has been crossed until this threshold has been crossed for several periods 250 of the charging field. This is desirable to prevent algorithm 71 progression in case of a "glitch" or some passing transient that causes Vcoil to be less than Vt for an insignificant time or number of periods. Thus, for example, the algorithm 71 may progress only if Vcoil<Vt for three consecutive periods.

An issue with this approach for determining the vicinity of the IPG 110 to the external charger 150 is that other conductive structures aside from the IPG 110 may also cause Vcoil to be less than Vt. For example, if the external charger 150 is sitting on or near a metallic structure, such as a metallic table or chair, the on/off algorithm 71 might conclude that the IPG 110 is in vicinity when it is not. Subsequent steps of the on/off algorithm 71 deal with this issue by seeking confirmation that the IPG 110 is indeed in the vicinity of the external charger 150 and able to be charged, as opposed to some other conductive structure.

Although not strictly necessary, at this point the on/off algorithm 71 may alert the user that the external charger 150 believes the IPG 110 to be in its vicinity (step 204). Issuing such a user alert can be beneficial for a number of reasons. First, it allows the user to move the external charger 150 away from an interfering conductive structure that might be falsely causing the alert, for example, away from the metal table on which it is sitting. As will be discussed further below, alerting the user in this manner to move the external charger 150 can prevent the on/off algorithm 71 from needlessly progressing to subsequent steps that could result in generation of a significant charging field, and thus waste energy in the external charger 150. Second, if the IPG 110 is actually in the vicinity of the external charger 150 and if charging is desired, the alert can notify the user to take certain steps to allow charging to begin, as discussed further below. The user alert can take forms similar to the indications issued by the alignment indicator 78 to notify the user about misalignment during a regular charging session, such as lighting an LED 62 on the external charger 150, or issuing sounds from a speaker (not shown), etc.

Figure 9:
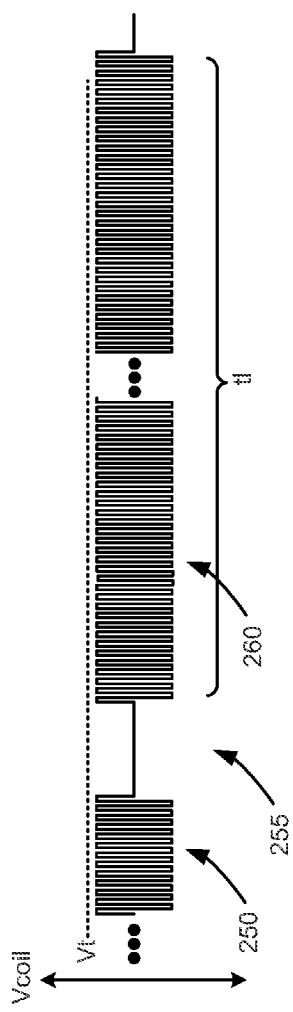
FIG. 9 shows a charging field during a listening window that issues after the external charger senses proximity to the IPG or other conductive structure.

In next steps, the external charger 150 seeks to verify whether the IPG 110 is actually in its vicinity (as opposed to some other conductive structure) by generating a charging field during a listening window 260 (step 206), as shown in FIG. 9. The listening window 260 can have a duration t1 of about 20 second for example. During the listening window, the LSK demodulator 74 in the external charger 150 looks for an indication whether the IPG 110 is in its vicinity, and such indication can be provided in a number of ways. As shown in FIG. 6, a first indication can comprise an LSK reply from the IPG 110 (step 208), and a second indication can comprise a signature indicative of predictable movement of the external charger by the user (step 214). While both of these indications are not strictly necessary, they are desired in the on/off algorithm 71 in light of the possibility that the battery 14 in the IPG 110 may be so depleted that the IPG 110 is essentially non-functional, as discussed further below.

Figure 10:
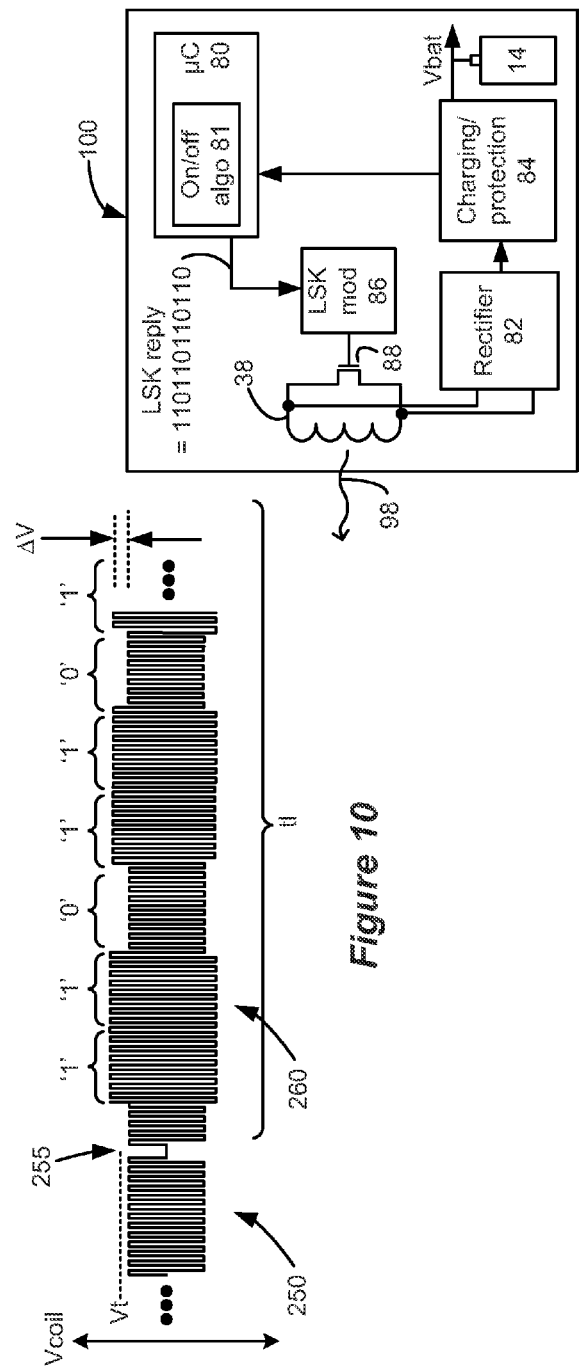
FIG. 10 shows the IPG issuing a Load Shift Keying (LSK) reply signal in response to the charging field received during the listening window.

The first of these indications—LSK reply—is shown in FIG. 10. During the listening window 260, the IPG 110 receives the charging field 96 via the coil 38, rectifier 82, and charging/protection circuitry 84, the latter of which can notify the on/off algorithm 81 in the IPG's control circuitry 80 of such receipt. In response, the on/off algorithm 81 can issue an LSK reply signal, which can be demodulated 74 at the external charger 150 to inform the external charger that the IPG 110 is truly in its vicinity (step 208) and that a normal charging session can commence (step 212). The LSK reply signal can take many forms, but should be distinct from other LSK signals, such as stop charging signal 01010101 . . . discussed in the Background. In the illustrated example, the reply signal comprises 110110110110, i.e., three repeating unit of '110.' This is desired to give the LSK reply signal a different periodicity than the stop charging signal, thus allowing the LSK demodulator 74 in the external charger 150 to more easily differentiate between the two. Other differentiable LSK reply signals could be used, and the illustrated signal should be understood as merely one example.

Note that the on/off algorithm 81 in the IPG 110 can be programmed to issue the LSK reply signal whenever the IPG 110 first acknowledges receipt of a charging field 96. The external charger 150 can provide a gap 255 between its last period 250 and the start of the listening window 260, as shown in FIG. 9. The charging field 96 will cease during this gap 255, thus ensuring that the IPG 110 will see a new issuance of a charging field during the listening window 260, and can issue the LSK reply signal at that time. Alternatively, the on/off algorithm 81 in the IPG 110 can ignore charging fields of short duration, such as during the periods 250, so that LSK reply signals will not needlessly issue during such periods.

The effect of LSK reply signal on Vcoil during the listening window 260 is shown in FIG. 10, with '1' bits causing an increase ($\Delta V$) in Vcoil. The on/off algorithm 81 in the IPG can issue each of the LSK bits for 1 millisecond for example, and thus the entire 12-bit string of the LSK reply signal only takes 12 milliseconds to issue. The LSK demodulator 74 is assisted in its demodulation task by knowing the duration of the bits in the LSK reply signal, as this will make relevant variations in Vcoil easier to identify. The LSK reply signal can issue from the IPG 110 repeatedly, for example every second, thus allowing 20 such signals to issue during the 20-second listening window 260, and increasing the likelihood that the external charger 150 will adequately receive the signal at least once. Once the demodulator 74 determines whether a LSK reply signal has been received during the listening window 260, it notifies the on/off algorithm 71 in the external charger 150 of this fact, so that next steps can be taken. To guard against inadvertent detection of the IPG, the demodulator 74 may only indicate receipt of the reply signal to the on/off algorithm 71 if a number of LSK reply signal are received in a row (for example, three), meaning that the demodulator 74 in this example would need three seconds to make this determination. Once the demodulator 74 indicates receipt of a reply signal, the on/off algorithm 71 can end the listening window (step 206), and next steps can be taken.

Upon receipt of the LSK reply signal, the on/off algorithm 71 can be certain that the IPG is in its vicinity, and the user alert issued earlier (if any; step 204) can be extinguished (step 210). Thereafter, on/off algorithm 71 can continue issuing a charging field 96 to charge the IPG 110 during a normal charging session (step 212), such as is discussed in the Background. Note that continuing the charging field 96 between steps 206 and 212 without a gap will keep the on/off algorithm 81 in the IPG from issuing a new LSK reply signal. However, this is not strictly necessary, and instead the charging field can cease prior to step 212. Even if the charging field is continuous between steps 206 and 212, the charging fields generated during these steps can be described as separate charging fields.

During this normal charging session (step 212), the coupling circuitry 76 and alignment indicator 78 can operate as normal to inform the user whether to adjust positioning of the external charger 150 relative to the IPG 110, and the on/off algorithm 81 can issue the stop charging signal (01010101 . . . ) to inform the on/off algorithm 71 in the IPG 110 when charging can cease. Other events can occur during the normal charging session of step 212 as well, such as adjustment of the intensity of the charging field 96 (i.e., adjustment of Icoil), or adjustment of the duty cycle of the charging field (which may be necessary to control heating). See U.S. Patent Application Publication 2011/0087307, discussing such details at length. Once charging has ceased, and ignoring counter X for the moment (step 230), the external charger 150 can revert back to standby mode (step 200) in preparation for locating and charging the IPG at some future time.

It may be possible that the IPG 110, even if in the vicinity of the external charger 150, is so depleted that it is not able to operate its LSK circuitry to communicate a LSK reply signal back to the external charger 150 during the listening window 260. In this circumstance, the demodulator 74 can assess whether a second indication is present indicating the vicinity of the IPG 110, as shown in FIGS. 11A and 11B.

This second indication relies on user manipulation of the external charger 150 relative to the IPG 110 during the listening window 260. As shown in FIG. 11A, the user moves the external charger 150 between a position A close to the IPG 110 and a position B away from the IPG 110. Position A might comprise the placing the external charger 150 on the patient's tissue 25 proximate the IPG 110, while position B might comprise moving the external charger 150 an arm's length away from the IPG 110.

Providing this type of indication to the external charger 150 requires previous training of the user, either by the user's clinician, user manuals accompanying the system, or other means. For example, a user desiring to charge of his IPG 110 can be instructed with the following movement procedure: place the external charger in position A (against his IPG 110) for five seconds, then move it to position B (away) for two seconds, then back to position A for two seconds, then back to position B for two seconds, etc. The user can be instructed to continue this cyclic movement pattern for about 20 seconds, i.e., the duration t1 of the listening window 260.

If user alerts are used (step 204), such alerts can inform the user how far he has to engage in this movement procedure. For example, when the user places the external charger 150 in position A for five seconds, Vcoil would be less than Vt (step 202), and an alert would issue (step 204). The listening window 260 would be started during which a charging field is generated (step 206). If the battery 14 in the IPG 110 is sufficiently charged to detect the charging field and provide LSK communications, the external charger 150 should receive a LSK reply signal in the first five seconds, as described above. This would extinguish the alert (step 210), and begin the charging session (step 212). Seeing that the alert has been extinguished (step 210), the user would know that he didn't need to continue the movement procedure, and that he could simply leave the external charger in position A. If the alert is not extinguished (step 210), the user would know that the IPG battery 14 is significantly depleted, and to continue the movement procedure by moving the external charger 150 to position A, then back to B, etc. for the duration of the listening window 260, or at least until the movement signature has been received (step 214) and the alert is later extinguished (at step 216), as discussed further below.

If user alerts do not comprise part of the on/off algorithm 71, the user can simply be instructed to engage in the full movement procedure. In this scenario, it is possible that an LSK reply signal will have been sent once the external charger 150 is placed initially in position A, but the user would not know this, and so would engage in the full movement procedure to cover the possibility that the IPG was so depleted as to be inoperative. Although the full movement procedure might not be necessary, it would be harmless: if an LSK reply signal had been received, and charging had already begun (step 212) unbeknownst to the user, moving the external charger away from the implant (position B) would simply mean the implant is not receiving a charge during these relatively short periods. Indeed, the coupling circuitry 76 and alignment indicator 78 may be useful to notify the user of this fact, i.e., that a charging session had begun (step 212), and that continuing further with the movement procedure is unnecessary.

Indication that the movement procedure has been performed during the listening window 260, and thus that the IPG 110 must truly be present (as opposed to some other conductive structure), occurs when the demodulator 74 detects the movement signature illustrated in FIG. 11B. As shown, the coil voltage, Vcoil, is smaller when the external charger 150 is in position A close to the IPG 110, and is larger when in position B away from the IPG. This change in Vcoil ($\Delta V$) results from the difference in mutual inductance that the external charger 150 sees relative to the IPG 110 in the two positions, as should be clear from earlier discussion. The demodulator 74 can detect this movement signature, knowing in advance how long the user has been instructed to hold the external charger in positions A (tA) and B (tB). (tA and tB can be different, although this example assume they are both about 2 seconds). One skilled will understand that the demodulator 74 may need to integrate or average Vcoil to determine whether it is changing with a periodicity matching the movement procedure, which determination can be made even in advance of the end of the listening window 260. Note that the periodicity generated in Vcoil due to changes in position (FIG. 11B) occurs on a much greater time scale (seconds versus millisecond) than changes resulting from LSK telemetry (FIG. 10). As such, the demodulator 74 can determine without confusion whether LSK telemetry is present (step 208), or if the movement procedure is occurring (step 214), and thus can inform either indication to the on/off algorithm 71.

Once the demodulator 74 has determined that the IPG 110 is present based upon the movement signature of FIG. 11B, and has notified the on/off algorithm 71 of this fact (step 214), the on/off algorithm 71 can conclude that the IPG is present, but must be significantly depleted. At this point, user alerts can be extinguished (if any; step 216), and the external charger 150 can continue generating a charging field 96 for a set period (step 218). Note that continuing the charging field 96 between steps 206 and 218 without a gap will keep the on/off algorithm 81 in the IPG from issuing a new LSK reply signal. However, this is not strictly necessary, and instead the charging field can cease prior to step 218. Even if the charging field is continuous between steps 206 and 218, the charging fields generated during these steps can be described as separate charging fields. This set period in step 218 is preferably long enough to sufficiently charge the IPG's battery 14 to allow the IPG 110 to once again engage in LSK communications, even if not fully charged. This set time period may vary between applications, depending for example on the depth of the IPG 110 in the patient's tissue 25. However, in one example, the set time period for charging in step 218 can comprise 15 minutes.

Ignoring counter X for a moment (step 230), once charging for the set time period has finished (step 218), the on/off algorithm 71 returns to the standby mode (step 200). Charging of the IPG's battery 14 may however not be complete, and so the algorithm 71 essentially repeats: if Vcoil is low, suggesting external charger vicinity to the IPG (step 202), a charging field is issued during a new listening window (step 206). If the IPG has been sufficiently charged to allow for LSK communications and an LSK reply signal is received (step 208), charging can occur as normal until the battery 14 is fully charged (step 212). If the battery 14 is still depleted and LSK communications are still not functional, the user can be prompted to engage in the movement procedure again (step 214) to charge the IPG 110 for another set time period (step 218), etc.

As noted earlier, other conductive structures in the vicinity of the external charger 150 (aside from the IPG 110) may also signify coupling, and cause Vcoil to be less than Vt (step 202). In this scenario, the external charger 150 would not receive an LSK reply signal (step 208), nor would it be likely to receive a movement signature (step 214). In such a case, it is not desirable for the external charger 150 to generate significant charging fields 96 merely because the external charger might be proximate to the IPG 110. To handle this scenario, a counter X in employed in the on/off algorithm 71. Essentially, counter X counts how many times this scenario occurs, and if a maximum is exceeded, then the on/off algorithm 71 reverts to a standby mode in which the absolute value of Vcoil is ignored. This keeps the external charger 150 from needlessly issuing listening windows 260 (step 206), and wasting power during such windows by generating a charging field, merely because significant coupling is indicated.

As shown in FIG. 6, if neither an LSK reply (step 208) nor a movement signature (step 214) are detected by the demodulator 74 at the end of the listening window 260, user alerts are extinguished (if present; step 220), and the current value of the counter X is compared to a maximum. In the depicted example, this maximum is three, although this could vary. Assume currently that X=0. Because X is less than three (step 222), the counter X is incremented to 1 (step 228), and the standby mode is entered (step 200). If the external charger 150 is still proximate a conductive object (Vcoil<Vt; step 202), the algorithm 71 will repeat, and once again determine that neither an LSK reply nor a movement signature have been detected. X will thus be incremented to 2 (step 228), and the process will again repeat, until X=3 (step 222). At this point, the external charger 150 has tried three times to receive a reliable indication that the IPG is in its vicinity.

Having determined that this has not occurred, the external charger 150 will infer that it must be proximate some conductive structure other than the IPG 110. For example, it may be sitting on top of a metal table. In this case, the on/off algorithm 71 enters a second standby state (step 224), which similarly to the first standby state (step 200), will periodically (e.g., for 1 millisecond every second) generate a charging field 96. However, further comparisons of Vcoil to Vt during the periods are ignored (see, e.g., step 204), and instead the algorithm 71 simply assesses whether Vcoil significantly changes in magnitude (step 226). If Vcoil has not significantly changed, for example because the external charger 150 is still just sitting on the metal table, the algorithm 71 stays in the standby mode (step 224) and continues to assess Vcoil (step 226). If Vcoil has significantly changed, the algorithm 71 infers that the external charger 150's position has changed; perhaps the user has moved the external charger 150 away from the metal table, possibly because he was notified by alerts issued earlier (if any; step 204). Experience can teach what comprises a significant change in Vcoil. In one example, a change of 5% in the magnitude of Vcoil can indicate a significant positional change of the external charger in step 226.

Given the significance of this positional change, the counter X is set to 0 (step 230), and the first standby mode (step 200) is once again entered. If no conductive structures (including the IPG) are present, Vcoil will be greater than Vt, and the algorithm 71 will merely remain in the standby mode (step 200). If some conductive structure is detected (Vcoil<Vt; step 202), the algorithm 71 will continue as outlined above: if either an LSK reply (step 208) or a movement signature (step 214) is detected, some charging (either steps 212 or 218) will take place. Note that after charging has occurred (steps 212 or 218), the counter X is reset to 0 (step 230), because there is no concern at this time that the external charger 150 is not actually proximate to the IPG 110. If neither an LSK reply or a movement signatures is detected, meaning the external charger is still proximate some conductive structure other than the IPG 110, the counter X is incremented (step 228), and if the external charger 150 is not moved, the on/off algorithm 71 will once again enter the second standby mode (step 224) until the situation clears.

One skilled in the art will recognize that modifications to the disclosed technique are possible, and that the illustrated embodiments are merely examples. For example, while the LSK demodulator 74 and coupling detector 76 have been shown for convenience as separate circuit blocks, they could be integrated together into a single circuit block which assesses Vcoil for all purposes, including coupling (step 202), or whether an LSK reply or movement signature have been received (steps 208, 214). Moreover, these blocks 74 and 76 can issue data to the control circuitry 70, and the on/off algorithm 71, in different ways. For example, they can issue the coil voltage, Vcoil, leaving it to the on/off algorithm 71 to make the determinations required for the disclosed technique. Alternatively, the logic necessary to make these determinations can be present in the circuit blocks 74 and 76, in which case these blocks need merely indicate the results of those determination to the on/off algorithm 71 for action. Moreover, the circuit blocks 74 and 76 can be incorporated into the control circuitry 70 itself. In such an embodiment, Vcoil may only need to be digitized at a suitable rate (e.g., with an A/D converter) and sent to the control circuitry 70, which in turn would be programmed to perform the functions of the LSK demodulator 74 and the coupling detector 76, and make necessary determinations. The functionality of LSK demodulator 74 and coupling detector 76 can generally be considered as "detection circuitry."

While much of the disclosed technique centered around assessment of Vcoil, this is not strictly necessary. Assessment of Vcoil is sensible if a constant AC charging current, Icoil, is issued by the amplifier 72. However, the amplifier 72 may also issue a constant AC voltage signal, Vcoil, to generate the charging fields 96, in which case Icoil would be the interesting parameters to assess, in particular how Icoil changes in light of changes in mutual inductance provided by the existence conductive structures, LSK telemetry, etc. In short, any useful parameter of the charging coil 52 can be used as the basis for making the determinations in the disclosed technique.

Moreover, while preferred that the on/off algorithm 71 listens both for an LSK reply signal and a movement signature to cover the possibility that LSK communications might not be functional, the algorithm can be implemented by listening for only one of these two indications. It is also not strictly necessary that the on/off algorithm 71 use a counter or other measures to prevent inadvertent charging (steps 200 et seq.) in the event that an implant is not proximate to the charger, although this is desirable for power savings.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for charging a battery in an implantable medical device using an external charger, comprising:
   (a) generating a first magnetic field from a first coil at the external charger to automatically determine that the implantable medical device is possibly proximate the external charger by comparing a parameter of the first coil to a threshold value;

(b) upon determining that the external charger is possibly proximate the implantable medical device, automatically generating a second magnetic field from the first coil in the external charger;

(c) receiving at the external charger and during the second magnetic field at least one indication from the implantable medical device; and (d) upon receiving the at least one indication, automatically generating a third magnetic field from the first coil in the external charger to wirelessly charge the battery in the implantable medical device.

2. The method of claim 1, wherein automatically determining that the implantable medical device is possibly proximate the external charger occurs during one or more of the first magnetic fields.

3. The method of claim 2, wherein determining that the implantable medical device is possibly proximate the external charger comprises determining a parameter of the first coil during one or more of the first magnetic fields.

4. The method of claim 3, wherein the parameter comprises a magnitude of a voltage or current of the first coil.

5. The method of claim 3, wherein it is determined that the implantable medical device is possibly proximate the external charger upon the parameter crossing a threshold.

6. The method of claim 1, wherein the second magnetic field is generated for a set time period.

7. The method of claim 1, wherein the indication comprises a variation in a parameter of the first coil voltage.

8. The method of claim 7, wherein the variation in the parameter of the first coil voltage results from transmitting a reply signal from the implantable medical device.

9. The method of claim 8, wherein the reply signal is periodically transmitted from the implantable medical device during the second charging field.

10. The method of claim 8, wherein the implantable medical device has a second coil for receiving the second magnetic field, and wherein the reply signal is transmitted by modulating an impedance of the second coil.

11. The method of claim 10, wherein the second coil receives at least the third magnetic field to wirelessly charge the battery in the implantable medical device.

12. The method of claim 7, wherein the variation in the parameter of the first coil voltage results from moving the external charger relative to the implantable medical device.

13. The method of claim 12, wherein the external charger is cyclically moved to and from implantable medical device.

14. The method of claim 1, wherein the external charger can receive first and second indications during the second magnetic field.

15. The method of claim 14, wherein the first indication indicate that the IPG's battery is not depleted, and wherein the second indication indicates that the IPG's battery is depleted.

16. The method of claim 15, wherein if the first indication is received, the third magnetic field continues until the battery in the implantable medical device has been fully charged, and wherein if the second indication is received, the third magnetic field continues for a set time period.

17. The method of claim 1, further comprising:
(e) returning to step (a).

18. An external charger for charging a battery in an implantable medical device, comprising:
a coil;
driver circuitry configured to energize the coil to generate a magnetic field;
detection circuitry configured to measure a parameter of the coil while it is energized;
control circuitry coupled to the driver circuitry and the detection circuitry; and
an algorithm associated with the control circuitry, wherein the algorithm is configured to
energize the coil to generate a first magnetic field,
assess the measured parameter:
to determine if the implantable medical device is possibly proximate to the external charger by comparing the measured parameter to a threshold value, and if so,
to determine if at least one indication from the implantable medical device has been received, and if so to,
energize the coil to generate a second magnetic field to charge the battery in the implant.

19. The external charger of claim 18, wherein the algorithm determines if the implantable medical device is possibly proximate to the external charger by assessing a magnitude of a parameter of the coil while it is energized.

20. The external charger of claim 19, wherein the parameter comprises a magnitude of voltage or current of the coil while it is energized.

21. The external charger of claim 19, wherein the algorithm is programmed into the microcontroller.

22. The external charger of claim 18, wherein the algorithm determines whether the at least one indication from the implantable medical device has been received by assessing a variation in the measured parameter.

23. The external charger of claim 22, wherein the variation in the measured parameter comprises a serial stream of bits.

24. The external charger of claim 22, wherein the variation in the parameter indicates that the external charger has been moved relative to the implantable medical device.

25. The external charger of claim 22, wherein the variation in the parameter is cyclic.

26. The external charger of claim 18, wherein the algorithm is configured to assess the measured parameters to determine if a first or second indication from the implantable medical device has been received.

27. The external charger of claim 26, wherein if the first indication is received, the algorithm is configured to energize the coil to generate a magnetic field to charge the battery in the implant until the battery is fully charged.

28. The external charger of claim 26, wherein if the second indication is received, the algorithm is configured to energize the coil to generate a magnetic field to charge the battery in the implant for a set time period.

29. The external charger of claim 18, wherein the control circuitry comprises a microcontroller.

30. The external charger of claim 18, wherein the driver circuitry comprises an amplifier.

31. The external charger of claim 18, wherein the detection circuitry comprises an Load Shift Keying demodulator and a coupling detector.

32. The external charger of claim 18, wherein the external charger is hand-holdable.

33. The external charger of claim 18, wherein the driver circuitry is configured to energize the coil to generate a magnetic field at a single frequency.

34. The external charger of claim 18, further comprising an alignment detector to indicate external charger alignment to a user while the algorithm energizes the coil to generate a magnetic field to charge the battery in the implant.

* * * * *